US00PP10608P

United States Patent [19]

Zaiger et al.

[11] Patent Number: Plant 10,608

[45] Date of Patent: Sep. 22, 1998

[54] INTERSPECIFIC TREE "FLAVOR HEART"

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 631,284

[22] Filed: Apr. 8, 1996

[51] Int. Cl.[6] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of interspecific (plum×plum cot) tree. The genetic makeup of this interspecific hybrid is *Prunus salicina* X (*P. salicina*×*P. armenaica*). Its novelty consisting of the following unique combination of features that are desirable in a new variety:

1. Heavy and regular production of large size fruit.
2. Fruit with excellent flavor and eating quality.
3. Fruit with firm flesh, good handling and shipping quality.
4. Fruit holding firm on the tree 10 to 15 days after shipping ripe.
5. Fruit with an attractive dark ruby skin color.
6. Relatively uniform ripening of fruit throughout the tree.
7. Vigorous, semi-upright growth.

1 Drawing Sheet

ORIGIN OF THE VARIETY

The present new variety of interspecific tree was developed by us in our experimental orchard located near Modesto, Calif., as a first generation cross between two selected seedlings, field identification numbers 24EB412 and 4G1180. The maternal parent 24EB412 originated from an open pollinated seedling selection of Red Beaut Plum (U.S. Plant Pat. No. 2,539) crossed with an early maturing plum of unknown parentage. The Paternal parent 4G1180 (plum cot) originated from an open pollinated Red Beaut Plum (U.S. Plant Pat. No. 2,539) seed. We grew and maintained a large group of these first geneation seedlings, one such seedling, which is the present variety, being especially desirable with respect to its fruit, was selected for asexual reproduction and commercialization.

ASEXUAL REPRODUCTION OF THE VARIETY

Asexual reproduction by budding of the new and distinct variety of interspecific tree was performed by us in our experimental orchard located near Modesto, Calif., which shows that all characteristics of the new interspecific tree and its fruit are established and transmitted through succeeding propagations and come true to the original tree in all respects.

SUMMARY OF THE VARIETY

A new and distinct variety of interspecific tree which is of large size, vigorous, semi-upright growth and a productive and regular bearer of large, firm, clingstone fruit with excellent flavor and eating quality. The fruit is further characterized by having good handling and shipping quality, holding firm on the tree 10 to 15 days after shipping ripe, having relatively uniform ripening of fruit throughout the tree and having an attractive dark ruby skin color.

DESCRIPTION OF THE PHOTOGRAPH

The accompanying color photographic illustration shows typical specimens of the foliage and fruit of the present new interspecific variety with the upper and lower surface of the leaves being shown; an exterior and a cross sectional view of the fruit being divided in the suture plane to reveal flesh coloration, pit cavity and a stone remaining in place. The photographic illustration was taken shortly after being picked at maturity (shipping ripe) and the colors are as nearly true as is reasonably possible in a color representation of this type.

DESCRIPTION OF THE VARIETY

The botanical detailed description of the present interspecific variety, its flowers, foliage and fruit are based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Form.*—Semi-spreading.
- *Density.*—Medium dense.
- *Bearer.*—Regular.
- *Production.*—Productive.

Trunk:
- *Size.*—Large.
- *Texture.*—Medium shaggy.
- *Color.*—Brown to grayish brown. (5-E-5) to (5-F-5).

Branches:
- *Size.*—Medium.
- *Texture*—Smooth to medium rough, varies with age of growth.
- *Lenticels.*—Medium size. Medium number.
- *Color.*—Light brown to brown. (5-D-6) to (5-E-6).

Leaves:
- *Size.*—Large. Average length 5". Average width 2".
- *Surface.*—Smooth.
- *Form.*—Oblanceolate. Pointed.
- *Margin.*—Finely serrate.
- *Thickness.*—Medium.
- *Petiole.*—Average length — ¾". Average thickness — 1/16".
- *Glands.*—Number varies from 0 to 3. Average number 2. Globose. Medium Size. Located on upper portion of petiole and base of leaf blade.
- *Color.*—Upper surface — green to dark green (29-F-7) to (29F-8). Lower surface — light green to green (29-E-4) to (29-E-5).

Flower buds:
- *Size.*—Medium.

*Form.*—Plump.
*Length.*—Medium.

Flowers:
*Blooming period.*—Date of first bloom: Mar. 2, 1994. Date of full bloom: Mar. 8, 1994. Varies slightly with climatic conditions.
*Size.*—Medium.
*Pollen.*—Present.
*Color.*—White.

Fruit:
*Maturity when described.*—Firm ripe.
*Date of first picking.*—Aug. 3, 1994.
*date of last picking.*—Aug. 8, 1994.
*Size.*—Large. Average diameter axially 3 1/16". Average transversely in suture plane 2 5/8".
*Form.*—Elongated, heart shape, flattened at base, elongated near apex.
*Suture.*—Shallow, extends from base to apex.
*Base.*—Retuse.
*Cavity.*—Nearly rounded, only slightly elongated in suture plane. Average depth — 3/16". Average width — 1/4".
*Ventral surface.*—Rounded, nearly smooth.
*Stem.*—Average length 1/2". Average thickness 3/32".

Flesh:
*Ripens.*—Evenly.
*Texture.*—firm, meaty.
*Fibers.*—Small, tender.
*Flavor.*—Excellent, good balance between sugar and acid.
*Aroma.*—Slight.
*Eating quality.*—Excellent.
*Juice.*—Moderate.
*Color.*—Yellow to maize yellow (4-A-4) to (4-A-6). Yellowish white streaks (1-A-2) extending out from pit cavity toward skin surface. Surface of pit cavity, pale orange to grayish orange (5-B-4) to (5-B-6).

Skin:
*Thickness.*—Medium.
*Texture.*—Medium, tenacious to flesh.
*Down.*—Wanting.
*Bloom.*—Moderate.
*Tendency to crack.*—None.
*Color.*—Ground color lake red to garnet red (8-C-8) to (8-D-8). Overspread with dark ruby to dark magenta (12-F-7) to (13-F-3), except in small areas, randomly spaced speckling of ground color showing.

Stone:
*Type.*—Clingstone.
*Size.*—Medium. Average length 1 1/8". Average width 3/4". Average thickness 3/8".
*Form.*—Ovoid.
*Sides.*—Equal to unequal.
*Base.*—Usually straight, varies from straight to slightly rounded.
*Surface.*—Small shallow furrows toward apex, usually a shallow furrow on each side of suture, lightly pitted throughout.
*Tendency to split.*—None.
*Color.*—Light brown to reddish brown (8-C-5) to (8-C-8).

Use: Dessert.
*Market.*—Local and long distance.

Keeping quality: Good.

Shipping quality: Good.

The interspecific tree, its flowers, foliage and fruit herein described may vary in slight detail due to climate, soil conditions and cultural practices under which the variety may be grown; the present botanical description is that of the variety grown under the ecological conditions prevailing near Modesto, Calif.

We claim:

1. A new and distinct variety of interspecific tree, substantially as illustrated and described, characterized by its large size, vigorous, semi-speading growth and being a productive and regular bearer of large, firm, clingstone fruit with excellent flavor and eating quality; the fruit is further characterized by having good handling and shipping quality, relatively uniform ripening throughout the tree, holding firm on the tree 10 to 15 days after maturity (shipping ripe) and having an attractive dark ruby skin color.

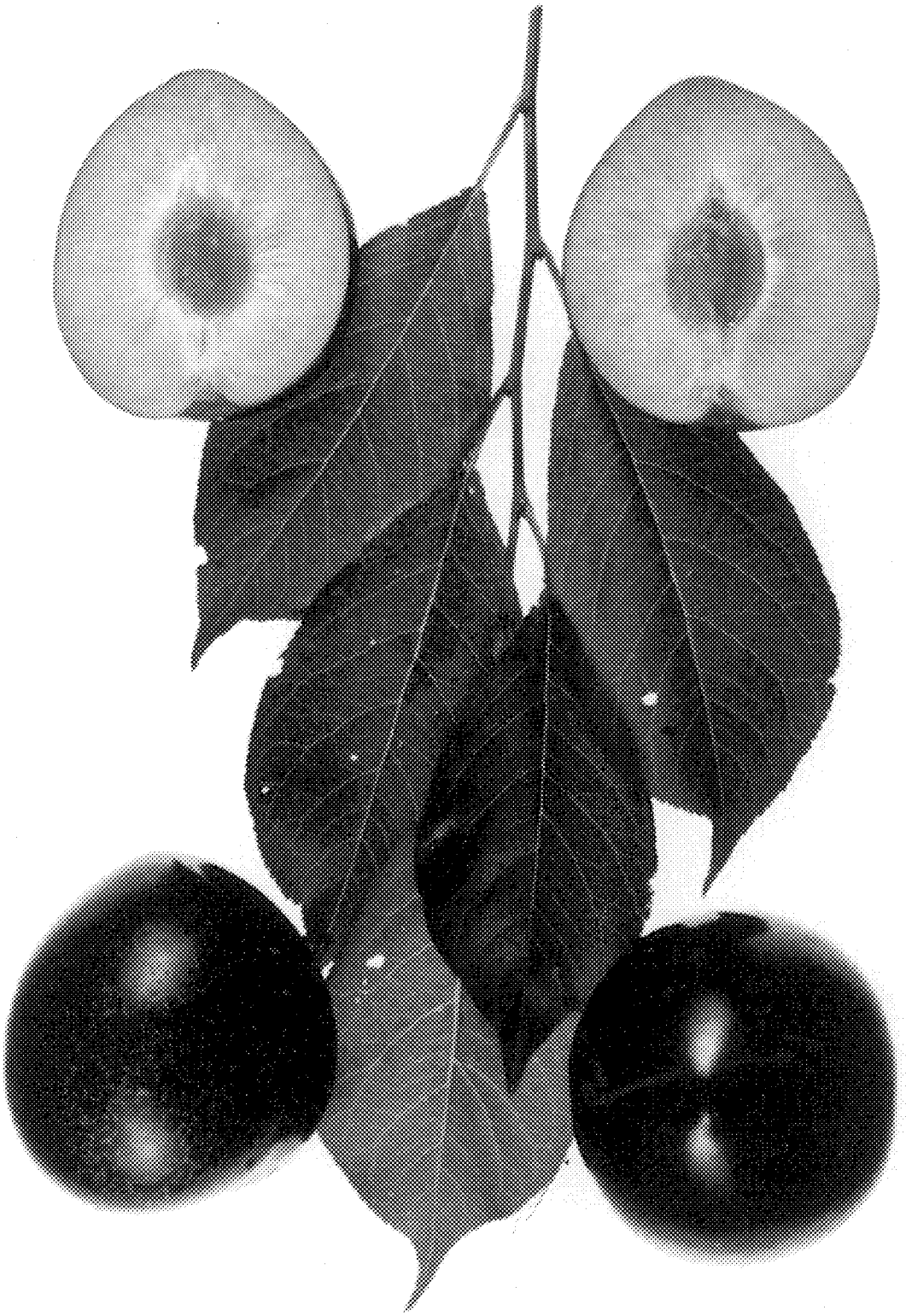

* * * * *